US005480998A

United States Patent [19]
Hamanaka et al.

[11] Patent Number: 5,480,998
[45] Date of Patent: Jan. 2, 1996

[54] OXIME DERIVATIVE

[75] Inventors: Nobuyuki Hamanaka; Kanji Takahashi; Hidekado Tokumoto, all of Osaka, Japan

[73] Assignee: Ono Pharmaceutical Co., Ltd., Osaka, Japan

[21] Appl. No.: 215,019

[22] Filed: Mar. 17, 1994

Related U.S. Application Data

[63] Continuation of Ser. No. 93,614, Jul. 20, 1993, abandoned.

[30] Foreign Application Priority Data

Jul. 21, 1992 [JP] Japan .................................. 4-215457

[51] Int. Cl.$^6$ ..................... C07D 213/30; C07D 213/42; C07D 213/53; C07D 213/54
[52] U.S. Cl. ........................... 546/333; 546/264; 560/35; 562/440
[58] Field of Search .............................. 562/440; 560/35; 546/264, 333; 514/332, 357, 539, 567

[56] References Cited

U.S. PATENT DOCUMENTS

| | | | |
|---|---|---|---|
| 4,352,804 | 10/1982 | van Zorge | 424/250 |
| 4,954,523 | 9/1990 | Yamagishi et al. | 514/521 |
| 4,971,985 | 11/1990 | Otsuka et al. | 514/357 |

FOREIGN PATENT DOCUMENTS

| | | | |
|---|---|---|---|
| 0013607 | 7/1980 | European Pat. Off. | |
| 004329 | 1/1982 | European Pat. Off. | |
| 0366006 | 5/1990 | European Pat. Off. | 546/333 |
| 0542203 | 5/1993 | European Pat. Off. | |
| 3504677 | 8/1986 | Germany | |

OTHER PUBLICATIONS

Chemical Abstracts, vol. 118, 1993, Columbus, Ohio, U.S.; Abstract No. 19130b.
Nature, vol. 263, pp. 663–665, Oct. 21, 1976, "An enzyme isolated from arteries transforms prostaglandin endoperoxides to an unstable substance that inhibits platelet aggregation", Moncada et al.
Prostaglandins, vol. 12, No. 5, pp. 685–713, Nov. 1976, "Arterial walls are protected against deposition of platelet thrombi by a substance (prostaglandin X) . . . endoperoxides", Gryglewski et al.
Prostaglandins, vol. 12, No. 6, pp. 915–928, Dec. 1976, "The chemical structure of prostaglandin X (prostacyclin)", Johnson et al.
Prostaglandins, vol. 13, No. 3, pp. 377–388, Mar. 1977, "Modulation of human platelet adenylate cyclase by prostacyclin (PGX)", Gorman et al.
Chemical & Engineering News, pp. 17–19, Dec. 20, 1976, "New compound shakes up prostaglandin ideas".
British Journal of Pharmacology, vol. 76, pp. 423–438, 1982, "Antagonism of the thromboxane–sensitive contractile systems of the rabbit aorta, dog saphenous vein and . . . trachea", Jones et al.
British Journal of Pharmacology, vol. 84, pp. 595–607, 1985, "Competitive antagonism at thromboxane receptors in human platelets", Armstrong et al.
British Journal of Pharmacology, vol. 102, pp. 251–259, 1991, "Octimibate, a potent non–prostanoid inhibitor, acts via the prostacyclin receptor" Merritt et al.
British Journal of Pharmacology, vol. 86, p. 643P, 1986, "Novel prostaglandin endoperoxide analogues which block thromboxane receptors and mimic prostacyclin" Armstrong et al.
Moffett et al., J. Het. Chem., 16, pp. 1459–1467 (1979).

Primary Examiner—José G. Dees
Assistant Examiner—Barbara S. Frazier
Attorney, Agent, or Firm—Sughrue, Mion, Zinn, Macpeak & Seas

[57] ABSTRACT

An oxime derivative (I):

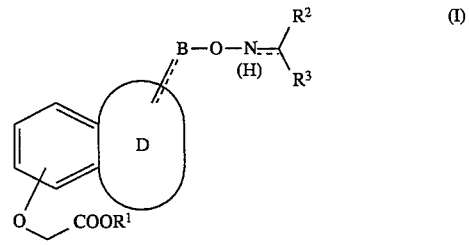

that D ring and B bonding to D ring are (i)–(iv), wherein $R^1$ is hydrogen, lower alkyl; $R^2$ is hydrogen, alkyl, phenyl, cycloalkyl, monocyclic ring containing nitrogen, lower alkyl substituted by benzene ring or cycloalkyl, lower alkyl substituted by monocyclic ring containing nitrogen; $R^3$ is alkyl, phenyl, cycloalkyl, monocyclic ring containing nitrogen, lower alkyl substituted by benzene ring or cycloalkyl, lower alkyl substituted by monocyclic ring containing nitrogen; e is 3–5, f is 1–3, p is 1–4, q is 1–2, r is 1–3; the position of the bond to D ring in (iii) and (iv) is a or b, and the ring in $R^2$ and $R^3$ may be substituted by lower alkyl, alkoxy, halogen, nitro, trihalomethyl; and salts thereof, possess an agonistic activity on PGl2 receptor, and therefore are useful for prevention and/or treatment of thrombosis, arteriosclerosis, ischemic heart diseases, gastric ulcer and hypertension.

14 Claims, No Drawings

OXIME DERIVATIVE

CROSS REFERENCE TO RELATED APPLICATION

This is a continuation of application No. 08/093,614, filed Jul. 20, 1993, now abandoned.

SUMMARY

This invention is related to an oxime derivative.

More particularly, this invention is related to:
1) an oxime derivative of the formula (I):

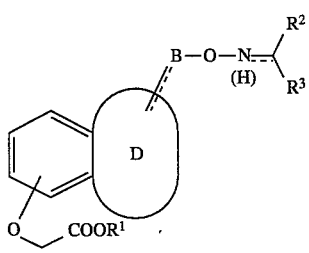

wherein all the symbols are the same meaning as hereafter defined, and non-toxic salts thereof,
2) processes for the preparation thereof and
3) pharmaceutical agents containing them as active ingredient.
4) methods of prevention and treatment by administering them to the patient to be treated.

BACKGROUND OF THE INVENTION

Prostaglandin $I_2$ ($PGI_2$) is a physiologically active natural substance having the following structural formula, which is biosynthesized from Prostaglandin $H_2$ ($PGH_2$) in the metabolic process in vivo called arachidonate cascade.

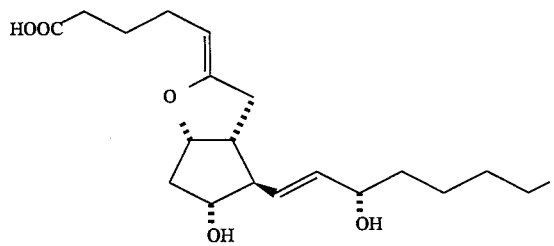

(see Nature, 263, 663(1976), Prostaglandins, 12, 685(1976), ibid, 12, 915(1976), ibid, 13, 375 (1977) and Chemical and Engineering News, Dec. 20, 17(1976)).

$PGI_2$ has been confirmed to possess not only a very strong inhibitory activity on blood platelet aggregation but an inhibitory activity on blood platelet adhesion, a vasodilating activity, an inhibitory activity on gastric acid secretion etc. Therefore, it has been considered that $PGI_2$ is useful for the prevention and/or the treatment for thrombosis, arteriosclerosis, ischemic heart diseases, gastric ulcer, hypertension etc. But its application for pharmaceuticals is limited because of its chemical instability and difficulty of separation of the actions according to purpose. Accordingly, various $PGI_2$ derivatives have been synthesized and much research has been carried out for the maintenance and the separation of the actions. However, we have not had satisfactory results yet.

Recently, in order to solve two problems above described, the research for $PGI_2$ receptor agonists which don't have PG skeleton has been carried out.

RELATED ARTS

It has been reported in the literatures, that the following compounds not having the $PGI_2$ skeleton are $PGI_2$ receptor agonists which bind to a $PGI_2$ receptor and inhibit blood platelet aggregation:

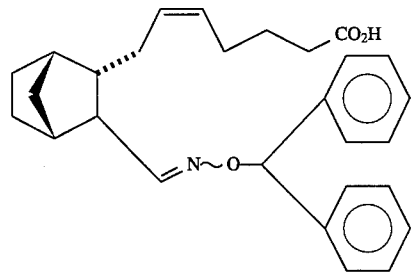

(see Brit. J. Pharmacol., 76, 423(1982), ibid, 84, 595(1985), ibid, Brit. J. Pharmacol. Proceedings Supplement, 86, 643P (1985), and the Japanese Patent Kohyo No. 55-501098),

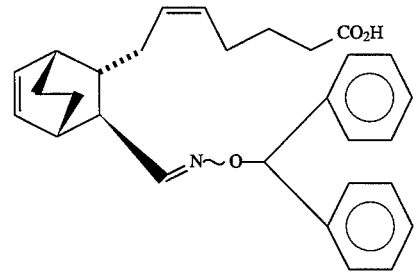

(see Brit. J. Pharmacol., 76, 423(1982), ibid, 84,595(1985), ibid, Brit. J. Pharmacol. Proceedings Supplement, 86, 643P (1985), and the Japanese Patent Kohyo No. 57-501127),

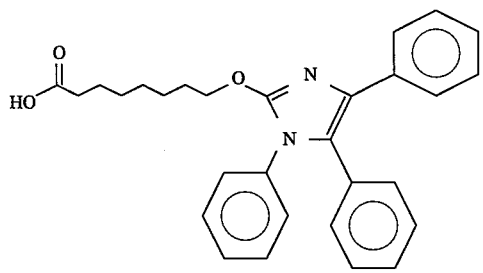

(see Brit. J. Pharmacol., 102, 251–266(1991) and the West German Patent Publication No. 3,504,677).

DISCLOSURE OF THE INVENTION

The present invention is related to:
1) oxime derivatives of the formula (I):

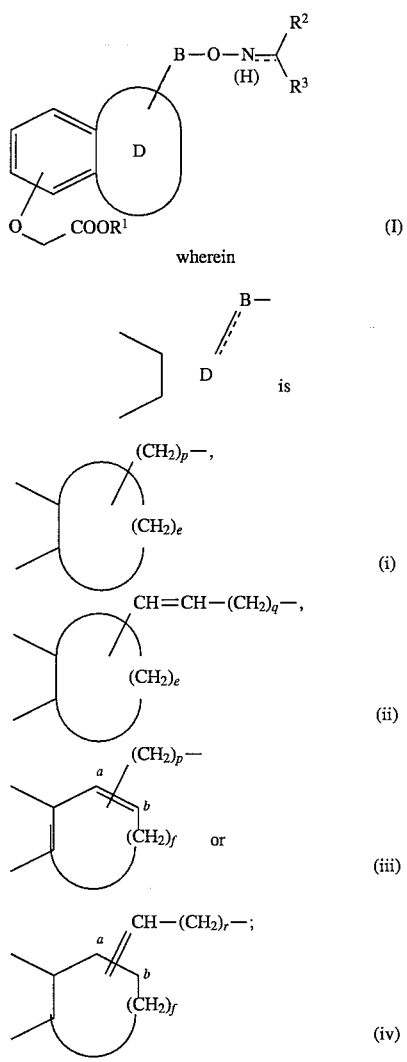

wherein

D is

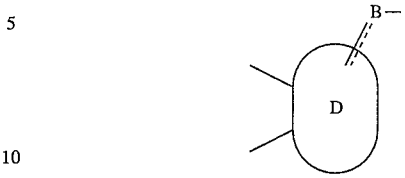

$R^1$ is hydrogen or C1–4 alkyl;
$R^2$ is
 (i) hydrogen,
 (ii) C1–8 alkyl,
 (iii) phenyl or C4–7 cycloalkyl,
 (iv) 4–7 membered monocyclic ring containing one nitrogen,
 (v) C1–4 alkyl substituted by benzene ring or C4–7 cycloalkyl or
 (vi) C1–4 alkyl substituted by 4–7 membered monocyclic ring containing one nitrogen;
$R^3$ is
 (i) C1–8 alkyl,
 (ii) phenyl or C4–7 cycloalkyl,
 (iii) 4–7 membered monocyclic ring containing one nitrogen,
 (iv) C1–4 alkyl substituted by benzene ring or C4–7 cycloalkyl or
 (v) C1–4 alkyl substituted by 4–7 membered monocyclic ring containing one nitrogen;

e is 3–5, f is 1–3, p is 1–4, q is 1 or 2, r is 1–3; with the proviso that, when is (iii) or (iv), —$(CH_2)_p$— and =$CH$-$(CH_2)_s$— is bonded at the position a or b on the ring, and the ring in $R^2$ and $R^3$ may be substituted by one to three of C1–4 alkyl, C1–4 alkoxy, halogen, nitro or trihalomethyl; and non-toxic salts thereof,
2) processes for the preparation thereof,
3) pharmaceutical compositions for the treatment of mammals, including humans, which comprises, as active ingredient, an effective amount of a compound of the formula (I), pharmaceutically acceptable salts thereof, pharmaceutically acceptable salts thereof and
4) methods for the treatment of mammals, including humans, which comprises, as active ingredient, an effective amount of a compound of the formula (I), pharmaceutically acceptable acceptable salts thereof. 3) pharmaceutical agents containing them as active ingredient.

Unless otherwise specified, all isomers are included in the invention. For example, alkyl, alkoxy, alkylene and alkenylene includes straight and branched ones. Double bond in alkenylene includes E, Z and EZ mixture. Isomers generated by asymmetric carbon(s) e.g. branched alkyl are included in the present invention.

Comparison With the Related Arts

The compounds of the present invention of formula (I) is novel compounds and it could not have been easily predicted that such type compounds have an activity of PGI2 receptor agonist.

Salt

The compounds of the formula (I) of the present invention, wherein $R^1$ is hydrogen may be converted into the corresponding salts by methods known per se. Non-toxic and water-soluble salts are preferable. Suitable salts are, for example, salts of alkaline metal (potassium, sodium etc.), salts of alkaline earth metal (calcium, magnesium etc.), ammonium salts, salts of pharmaceutically-acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

The compound of the formula (I) of the present invention may be converted into hydrate by conventional manner.

In the formula (I), C1–4 alkyl represented by $R^1$, $R^2$ and $R^3$ and substituents of the ring in $R^2$, $R^3$ means methyl, ethyl, propyl, butyl and isomeric groups thereof.

In the formula (I), C1–8 alkyl represented by $R^2$ and $R^3$ means methyl, ethyl, propyl, butyl, pentyl, hexyl, heptyl, octyl and isomedc groups thereof.

In the formula (I), C1–4 alkoxy as substituents in $R^2$ and $R^3$ means methoxy, ethoxy, propoxy, butoxy and isomeric groups thereof.

In the formula (I), halogen and halogen in trihalomethyl as substituents in $R^2$ and $R^3$ mean fluorine, chlorine, bromine and iodine atoms.

In the formula (I), C4–7 cycloalkyl represented by $R^2$ and $R^3$ means cyclobutyl, cyclopentyl, cyclohexyl and cyclopentyl.

In the formula (I), 4–7 membered monocyclic ring containing one nitrogen represented by $R^2$ and $R^3$ means azete, azole, pyridine, azepine rings and partially or fully saturated rings thereof.

Preferred Compounds

In the present invention of the formula (I), the following compounds and example compounds described hereinafter are preferred:

[5-[2-[1-phenyl-1-(3-pyridyl)methylideneaminooxy]ethyl]-5,6,7,8-tetrahydronaphthalen-1-yloxy]acetic acid,
[5-[2-[1-phenyl-1-(3-pyridyl)methylaminooxy]ethyl]-5,6,7,8-tetrahydronaphthalen-1-yloxy]acetic acid,
[5-[1-[1-phenyl-1-(3-pyridyl)methylideneaminooxy]methyl]-5,6,7,8-tetrahydronaphthalen-1-yloxy]acetic acid,
[6-[1-[1-phenyl-1-(3-pyridyl)methylideneaminooxy]methyl]-5,6,7,8-tetrahydronaphthalen-1-yloxy]acetic acid.
[5-[2-[1-pentyl-1-(3-pyridyl)methylideneaminooxy]ethyl]-5,6,7,8-tetrahydronaphthalen-1-yloxy]acetic acid,
[5-[2-[1-pentyl-1-(3-pyridyl)methylaminooxy]ethyl]-5,6,7,8-tetrahydronaphthalen-1-yloxy]acetic acid,
[5-[1-[1-pentyl-1-(3-pyridyl)methylideneaminooxy]methyl]-5,6,7,8-tetrahydronaphthalen-1-yloxy]acetic acid,
[6-[1-[1-pentyl-1-(3-pyridyl)methylideneaminooxy]methyl]-5,6,7,8-tetrahydronaphthalen-1-yloxy]acetic acid,
[5-[2-[1-cyclohexyl-1-(3-pyridyl)methylideneaminooxy]ethyl]-5,6,7,8-tetrahydronaphthalen-1-yloxy]acetic acid,
[5-[2-[1-cyclohexyl-1-(3-pyridyl)methylaminooxy]ethyl]-5,6,7,8-tetrahydronaphthalen-1-yloxy]acetic acid,
[5-[1-[1-cyclohexyl-1-(3-pyridyl)methylideneaminooxy]methyl]-5,6,7,8-tetrahydronaphthalen-1-yloxy]acetic acid,
[6-[1-[1-cyclohexyl-1-(3-pyridyl)methylideneaminooxy]methyl]-5,6,7,8-tetrahydronaphthalen-1-yloxy]acetic acid,
[5-[2-[1-cyclopentylmethyl-1-(3-pyridyl)methylideneaminooxy]ethyl]-5,6,7,8-tetrahydronaphthalen-1-yloxy]acetic acid,
[5-[2-[1-cyclopentylmethyl-1-(3-pyridyl)methylaminooxy]ethyl]-5,6,7,8-tetrahydronaphthalen-1-yloxy]acetic acid,
[5-[1-[1-cyclopentylmethyl-1-(3-pyridyl)methylideneaminooxy]methyl]-5,6,7,8-tetrahydronaphthalen-1-yloxy]acetic acid,
[6-[1-[1-cyclopentylmethyl-1-(3-pyridyl)methylideneaminooxy]methyl]-5,6,7,8-tetrahydronaphthalen-1-yloxy]acetic acid,
[5-[2-[1-benzyl-1-(3-pyridyl)methylideneaminooxy]ethyl]-5,6,7,8-tetrahydronaphthalen-1-yloxy]acetic acid,
[5-[2-[1-benzyl-1-(3-pyridyl)methylaminooxy]ethyl]-5,6,7,8-tetrahydronaphthalen-1-yloxy]acetic acid,
[5-[1-[1-benzyl-1-(3-pyridyl)methylideneaminooxy]methyl]-5,6,7,8-tetrahydronaphthalen-1-yloxy]acetic acid,
6-[1-[1-benzyl-1-(3-pyridyl)methylideneaminooxy]methyl]-5,6,7,8-tetrahydronaphthalen-1-yloxy]acetic acid,
5-[2-[1-phenyl-1-(4-pyridyl)methylideneaminooxy]ethyl]-5,6,7,8-tetrahydronaphthalen-1-yloxy]acetic acid,
[5-[2-[1-phenyl-1-(4-pyridyl)methylaminooxy]ethyl]-5,6,7,8-tetrahydronaphthalen-1-yloxy]acetic acid,
[5-[1-[1-phenyl-1-(4-pyridyl)methylideneaminooxy]methyl]-5,6,7,8-tetrahydronaphthalen-1-yloxy]acetic acid,
[6-[1-[1-phenyl-1-(4-pyridyl)methylideneaminooxy]methyl]-5,6,7,8-tetrahydronaphthalen-1-yloxy]acetic acid,
[5-[2-[1-phenyl-1-(3-pyridylmethyl)methylideneaminooxy]ethyl]-5,6,7,8-tetrahydronaphthalen-1-yloxy]acetic acid,
[5-[2-[1-phenyl-1-(3-pyridylmethyl)methylaminooxy]ethyl]-5,6,7,8-tetrahydronaphthalen-1-yloxy]acetic acid,
[5-[1-[1-phenyl-1-(3-pyridylmethyl)methylideneaminooxy]methyl]-5,6,7,8-tetrahydronaphthalen-1-yloxy]acetic acid,
[6-[1-[1-phenyl-1-(3-pyridylmethyl)methylideneaminooxy]methyl]-5,6,7,8-tetrahydronaphthalen-1-yloxy]acetic acid,
5-[2-[1-phenyl-1-(3-pyrrolylmethyl)methylideneaminooxy]ethyl]-5,6,7,8-tetrahydronaphthalen-1-yloxy]acetic acid,
5-[2-[1-phenyl-1-(3-pyrrolylmethyl)methylaminooxy]ethyl]-5,6,7,8-tetrahydronaphthalen-1-yloxy]acetic acid,
5-[1-[1-phenyl-1-(3-pyrrolylmethyl)methylideneaminooxy]methyl]-5,6,7,8-tetrahydronaphthalen-1-yloxy]acetic acid,
6-[1-[1-phenyl-1-(3-pyrrolylmethyl)methylideneaminooxy]methyl]-5,6,7,8-tetrahydronaphthalen-1-yloxy]acetic acid,
5-[3-[1-phenyl-1-(3-pyridyl)methylideneaminooxy]-1-propenyl]-5,6,7,8-tetrahydronaphthalen-1-yloxy]acetic acid,
5-[3-[1-phenyl-1-(3-pyridyl)methylaminooxy]-1-propenyl]-5,6,7,8-tetrahydronaphthalen-1-yloxy]acetic acid,
[6-[3-[1-phenyl-1-(3-pyridyl)methylideneaminooxy]-1-propenyl]-5,6,7,8-tetrahydronaphthalen-1-yloxy]acetic acid,
[5-[3-[1-pentyl-1-(3-pyridyl)methylideneaminooxy]-1-propenyl]-5,6,7,8-tetrahydronaphthalen-1-yloxy]acetic acid,
[5-[3-[1-pentyl-1-(3-pyridyl)methylaminooxy]-1-propenyl]-5,6,7,8-tetrahydronaphthalen-1-yloxy]acetic acid,
[6-[3-[1-pentyl-1-(3-pyridyl)methylideneaminooxy]-1-propenyl]-5,6,7,8-tetrahydronaphthalen-1-yloxy]acetic acid,
[5-[3-[1-cyclohexyl-1-(3-pyridyl)methylideneaminooxy]-1-propenyl]-5,6,7,8-tetrahydronaphthalen-1-yloxy]acetic acid,
[5-[3-[1-cyclohexyl-1-(3-pyridyl)methylaminooxy]-1-propenyl]-5,6,7,8-tetrahydronaphthalen-1-yloxy]acetic acid,
[6-[3-[1-cyclohexyl-1-(3-pyridyl)methylideneaminooxy]-1-propenyl]-5,6,7,8-tetrahydronaphthalen-1-yloxy]acetic acid,
[5-[3-[1-cyclopentylmethyl-1-(3-pyridyl)methylideneaminooxy]-1-propenyl]-5,6,7,8-tetrahydronaphthalen-1-yloxy]acetic acid,
5-[3-[1-cyclopentylmethyl-1-(3-pyridyl)methylaminooxy]-1-propenyl]-5,6,7,8-tetrahydronaphthalen-1-yloxy]acetic acid,
6-[3-[1-cyclopentylmethyl-1-(3-pyridyl)methylideneaminooxy]-1-propenyl]-5,6,7,8-tetrahydronaphthalen-1oyloxy]acetic acid,
5-[3-[1-benzyl-1-(3-pyridyl)methylideneaminooxy]-1-propenyl]-5,6,7,8-tetrahydronaphthalen-1-yloxy]acetic acid,
5-[3-[1-benzyl-1-(3-pyridyl)methylaminooxy]-1-propenyl]-5,6,7,8-tetrahydronaphthalen-1-yloxy]acetic acid,
[6-[3-[1-benzyl-1-(3-pyridyl)methylideneaminooxy]-1-propenyl]-5,6,7,8-tetrahydronaphthalen-1-yloxy]acetic acid,
[5-[3-[1-phenyl-1-(4-pyridyl)methylideneaminooxy]-1-propenyl]-5,6,7,8-tetrahydronaphthalen-1-yloxy]acetic acid,
[5-[3-[1-phenyl-1-(4-pyridyl)methylaminooxy]-1-propenyl]-5,6,7,8-tetrahydronaphthalen-1-yloxy]acetic acid,
[6-[3-[1-phenyl-1-(4-pyridyl)methylideneaminooxy]-1-propenyl]-5,6,7,8-tetrahydronaphthalen-1-yloxy]acetic acid,
[5-[3-[1-phenyl-1-(3-pyridylmethyl)methylideneaminooxy]-1-propenyl]-5,6,7,8-tetrahydronaphthalen-1-yloxy]acetic acid,

[5-[3-[1-phenyl-1-(3-pyridylmethyl)methylaminooxy]-1-propenyl]-5,6,7,8-tetrahydronaphthalen-1-yloxy]acetic acid,

[6-[3-[1-phenyl-1-(3-pyridylmethyl)methylideneaminooxy]-1-propenyl]-5,6,7,8-tetrahydronaphthalen-1-yloxy]acetic acid,

[5-[3-[1-phenyl-1-(3-pyrrolylmethyl)methylideneaminooxy]-1-propenyl]-5,6,7,8-tetrahydronaphthalen-1-yloxy]acetic acid,

[5-[3-[1-phenyl-1-(3-pyrrolylmethyl)methylaminooxy]-1-propenyl]-5,6,7,8-tetrahydronaphthalen-1-yloxy]acetic acid, 6-[3-[1-phenyl-1-(3-pyrrolylmethyl)methylideneaminooxy]-1-propenyl]-5,6,7,8-tetrahydronaphthalen-1-yloxy]acetic acid,

[5-[2-[1-phenyl-1-(3-pyridyl)methylideneaminooxy]ethyl]-7,8-dihydronaphthalen-1-yloxy]acetic acid,

[5-[2-[1-phenyl-1-(3-pyridyl)methylaminooxy]ethyl]-7,8-dihydronaphthalen-1-yloxy]acetic acid,

[5-[1-[1-phenyl-1-(3-pyridyl)methylideneaminooxy]methyl]-7,8-dihydronaphthalen-1-yloxy]acetic acid,

[6-[1-[1-phenyl-1-(3-pyridyl)methylideneaminooxy]methyl]-7,8-dihydronaphthalen-1-yloxy]acetic acid,

[5-[2-[1-pentyl-1-(3-pyridyl)methylideneaminooxy]ethyl]-7,8-dihydronaphthalen-1-yloxy]acetic acid,

[5-[2-[1-pentyl-1-(3-pyridyl)methylaminooxy]ethyl]-7,8-dihydronaphthalen-1-yloxy] acetic acid,

[5-[1-[1-pentyl-1-(3-pyridyl)methylideneaminooxy]methyl]-7,8-dihydronaphthalen-1-yloxy]acetic acid,

[6-[1-[1-pentyl-1-(3-pyridyl)methylideneaminooxy]methyl]-7,8-dihydronaphthalen-1-yloxy]acetic acid,

[5-[2-[1-cyclohexyl-1-(3-pyridyl)methylideneaminooxy]ethyl]-7,8-dihydronaphthalen-1-yloxy]acetic acid,

[5-[2-[1-cyclohexyl-1-(3-pyridyl)methylaminooxy]ethyl]-7,8-dihydronaphthalen-1-yloxy]acetic acid,

[5-[1-[1-cyclohexyl-1-(3-pyridyl)methylideneaminooxy]methyl]-7,8-dihydronaphthalen-1-yloxy]acetic acid,

[6-[1-[1-cyclohexyl-1-(3-pyridyl)methylideneaminooxy]methyl]-7,8-dihydronaphthalen-1-yloxy]acetic acid,

[5-[2-[1-cyclopentylmethyl-1-(3-pyridyl)methylideneaminooxy]ethyl]-7,8-dihydronaphthalen-1-yloxy]acetic acid,

[5-[2-[1-cyclopentylmethyl-1-(3-pyridyl)methylaminooxy]ethyl]-7,8-dihydronaphthalen-1-yloxy]acetic acid,

[5-[1-[1-cyclopentylmethyl-1-(3-pyridyl)methylideneaminooxy]methyl]-7,8-dihydronaphthalen-1-yloxy]acetic acid,

[6-[1-[1-cyclopentylmethyl-1-(3-pyridyl)methylideneaminooxy]methyl]-7,8-dihydronaphthalen-1-yloxy]acetic acid,

[5-[2-[1-benzyl-1-(3-pyridyl)methylideneaminooxy]ethyl]-7,8-dihydronaphthalen-1-yloxy]acetic acid,

[5-[2-[1-benzyl-1-(3-pyridyl)methylaminooxy]ethyl]-7,8-dihydronaphthalen-1-yloxy] acetic acid,

[5-[1-[1-benzyl-1-(3-pyridyl)methylideneaminooxy]methyl]-7,8-dihydronaphthalen-1-yloxy]acetic acid,

[6-[1-[1-benzyl-1-(3-pyridyl)methylideneaminooxy]methyl]-7,8-dihydronaphthalen-1-yloxy]acetic acid,

[5-[2-[1-phenyl-1-(4-pyridyl)methylideneaminooxy]ethyl]-7,8-dihydronaphthalen-1-yloxy]acetic acid,

[5-[2-[1-phenyl-1-(4-pyridyl)methylaminooxy]ethyl]-7,8-dihydronaphthalen-1-yloxy]acetic acid,

[5-[1-[1-phenyl-1-(4-pyridyl)methylideneaminooxy]methyl]-7,8-dihydronaphthalen-1-yloxy]acetic acid,

[6-[1-[1-phenyl-1-(4-pyridyl)methylideneaminooxy]methyl]-7,8-dihydronaphthalen-1-yloxy]acetic acid,

[5-[2-[1-phenyl-1-(3-pyridylmethyl)methylideneaminooxy]ethyl]-7,8-dihydronaphthalen-1-yloxy]acetic acid,

[5-[2-[1-phenyl-1-(3-pyridylmethyl)methylaminooxy]ethyl]-7,8-dihydronaphthalen-1-yloxy]acetic acid,

[5-[1-[1-phenyl-1-(3-pyridylmethyl)methylideneaminooxy]methyl]-7,8-dihydronaphthalen-1-yloxy]acetic acid,

[6-[1-[1-phenyl-1-(3-pyridylmethyl)methylideneaminooxy]methyl]-7,8-dihydronaphthalen-1-yloxy]acetic acid,

[5-[2-[1-phenyl-1-(3-pyrrolylmethyl)methylideneaminooxy]ethyl]-7,8-dihydronaphthalen-1-yloxy]acetic acid,

[5-[2-[1-phenyl-1-(3-pyrrolylmethyl)methylaminooxy]ethyl]-7,8-dihydronaphthalen-1-yloxy]acetic acid,

[5-[1-[1-phenyl-1-(3-pyrrolylmethyl)methylideneaminooxy]methyl]-7,8-dihydronaphthalen-1-yloxy]acetic acid,

[6-[1-[1-phenyl-1-(3-pyrrolylmethyl)methylideneaminooxy]methyl]-7,8-dihydronaphthalen-1-yloxy]acetic acid,

[5-[2-[1-phenyl-1-(3-pyridyl)methylideneaminooxy]ethylidene]-5,6,7,8-tetrahydronaphthalen-1-yloxy]acetic acid,

[5-[2-[1-phenyl-1-(3-pyridyl)methylaminooxy]ethylidene]-5,6,7,8-tetrahydronaphthalen-1-yloxy]acetic acid,

[6-[2-[1-phenyl-1-(3-pyridyl)methylideneaminooxy]ethylidene]-5,6,7,8-tetrahydronaphthalen-1-yloxy]acetic acid,

[5-[2-[1-pentyl-1-(3-pyridyl)methylideneaminooxy]ethylidene]-5,6,7,8-tetrahydronaphthalen-1-yloxy]acetic acid,

[5-[2-[1-pentyl-1-(3-pyridyl)methylaminooxy]ethylidene]-5,6,7,8-tetrahydronaphthalen-1-yloxy]acetic acid,

[6-[2-[1-pentyl-1-(3-pyridyl)methylideneaminooxy]ethylidene]-5,6,7,8-tetrahydronaphthalen-1-yloxy]acetic acid.

[5-[2-[1-cyclohexyl-1-(3-pyridyl)methylideneaminooxy]ethylidene]-5,6,7,8-tetrahydronaphthalen-1-yloxy]acetic acid,

[5-[2-[1-cyclohexyl-1-(3-pyridyl)methylaminooxy]ethylidene]-5,6,7,8-tetrahydronaphthalen-1-yloxy]acetic acid,

[6-[2-[1-cyclohexyl-1-(3-pyridyl)methylideneaminooxy]ethylidene]-5,6,7,8-tetrahydronaphthalen-1-yloxy]acetic acid,

[5-[2-[1-cyclopentyl methyl-1-(3-Pyridyl)methylideneaminooxy]ethylidene]-5,6,7,8-tetrahydronaphthalen-1-yloxy]acetic acid,

[5-[2-[1-cyclopentylmethyl-1-(3-pyridyl)methylaminooxy]ethylidene]-5,6,7,8-tetrahydronaphthalen-1-yloxy]acetic acid,

[6-[2-[1-cyclopentylmethyl-1-(3-pyridyl)methylideneaminooxy]ethylidene]-5,6,7,8-tetrahydronaphthalen-1-yloxy]acetic acid,

[5-[2-[1-benzyl-1-(3-pyridyl)methylideneaminooxy]ethylidene]-5,6,7,8-tetrahydronaphthalen-1-yloxy]acetic acid,

[5-[2-[1-benzyl-1-(3-pyridyl)methylaminooxy]ethylidene]-5,6,7,8-tetrahydronaphthalen-1-yloxy]acetic acid,

[6-[2-[1-benzyl-1-(3-pyridyl)methylideneaminooxy]ethylidene]-5,6,7,8-tetrahydronaphthalen-1-yloxy]acetic acid,

[5-[2-[1-phenyl-1-(4-pyridyl)methylideneaminooxy]ethylidene]-5,6,7,8-tetrahydronaphthalen-1-yloxy]acetic acid,

[5-[2-[1-phenyl-1-(4-pyridyl)methylaminooxy]ethylidene]-5,6,7,8-tetrahydronaphthalen-1-yloxy]acetic acid,

[6-[2-[1-phenyl-1-(4-pyridyl)methylideneaminooxy]ethylidene]-5,6,7,8-tetrahydronaphthalen-1-yloxy]acetic acid,

[5-[2-[1-phenyl-1-(3-pyridylmethyl)methylideneaminooxy]ethylidene]-5,6,7,8-tetrahydronaphthalen-1-yloxy]acetic acid,

[5-[2-[1-phenyl-1-(3-pyridylmethyl)methylaminooxy]eth-ylidene ]-5,6,7,8 -tetrahydronaphthalen-1-yloxy]acetic acid, -[2-[1-phenyl-1-(3-pyridylmethyl)methylideneami-nooxy]ethylidene ]-5, 6,7,8 -tetrahydronaphthalen-1-yloxy]acetic acid,

[5-[2-[1-phenyl-1-(3-pyrrolylmethyl)methylideneami-nooxy]ethylidene]- 5,6,7,8-tetrahydronaphthalen-1-yloxy]acetic acid,

[5-[2-[1-phenyl-1-(3-pyrrolylmethyl)methylaminooxy]eth-ylidene]-5,6,7,8 -tetrahydronaphthalen-1-yloxy]acetic acid and

[6-[2-[1-phenyl-1-(3-pyrrolylmethyl)methylideneami-nooxy]ethylidene]- 5,6,7,8-tetrahydronaphthalen-1-yloxy]acetic acid.

Process for the Preparation

In the compounds of the present invention of the formula (I), compounds wherein $R^1$ is hydrogen, of the formula (Ia):

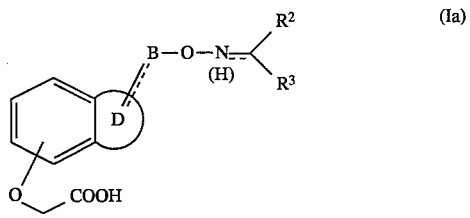

wherein all the symbols are the same meaning as hereinbefore defined, may be prepared by hydrolysis in an alkaline condition of a compound of formula (Ib):

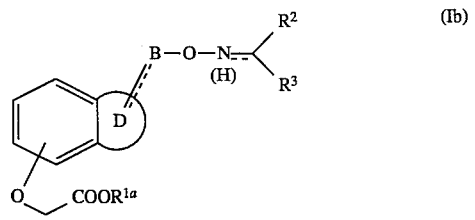

wherein $R^{1a}$ is C1–4 alkyl.

Hydrolysis of ester in an alkaline condition is known reaction, for example, it may be carried out in a water-miscible organic solvent (tetrahydrofuran, dioxan, ethanol, methanol, dimethoxyethane or two or more of the mixture thereof etc.), using an aqueous solution of alkali (sodium hydroxide, potassium hydroxide etc.), at −10° to 70° C.

In the compounds of the formula (Ib), compounds of the formula (Ib-1):

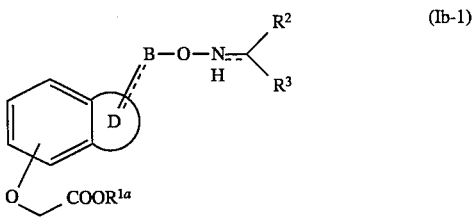

wherein all the symbols are the same meaning as hereinbefore defined, may be prepared by reduction of a compounds of formula (Ib-2):

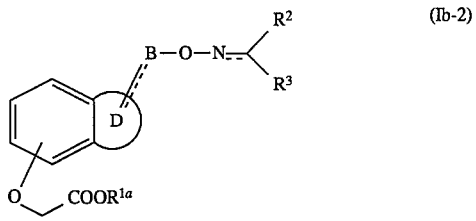

wherein all the symbols are the same meaning as hereinbefore defined.

Reduction of imino group into amino group is a known reaction, for example, it may be carried out in a water miscible organic solvent (tetrahydrofuran, dioxan, ethanol, methanol, dimethoxyethane or two or more of the mixture thereof etc.), in the presence of an acid (hydrochloric acid, acetic acid, trifluoroacetic acid etc.), using a reducing agent (sodium cyanoborohydride etc.), at 0° to 70° C.

Compounds of the formula (Ib-2) may be prepared by reacting a compound of formula (II):

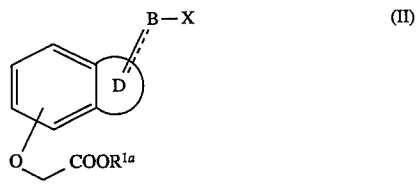

wherein X is halogen or mesyloxy, and the other symbols are the same meaning as hereinbefore defined, and a compound of formula (III):

wherein all the symbols are the same meaning as hereinbefore defined.

The reaction of halogenated alkyl and hydroxylamine is a known reaction, for example, it may be carried out in an inert organic solvent (dimethylformamide, hexamethylphos-phoramide, dimethoxyethane or two or more of the mixture etc.), in the presence of a base (sodium hydride, potassium t-butoxide, etc.), at 0° to 90° C.

The compounds of the formula (II) are known compounds, for example, they are disclosed in the specification of Japanese Patent Application No. 4- 209587. They may also be prepared by the series of reaction described in scheme A shown below.

In the scheme A, Ms is mesyl, $X^1$ and $X^2$ is independently halogen, and the other symbols are the same meaning as defined hereinbefore.

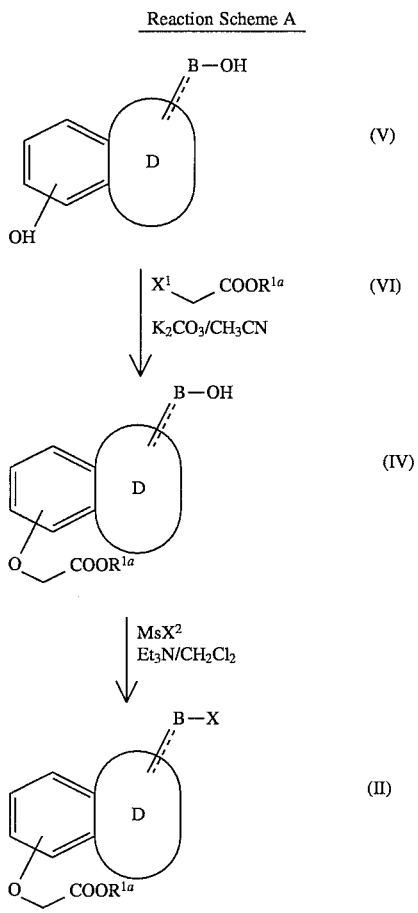

Reaction Scheme A

Starting Materials

The starting materials and each reagent in process for the preparation of the present invention are known per se, or may be prepared by methods known per se.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystalization. Purification may be carried out after each reaction, or after a series of reactions.

Pharmacological Activities

It has been confirmed that the compounds of the present invention of the formula (I) possess an agonistic activity on $PGI_2$ receptor by the following experimental results.

i) Inhibitory activity on binding of [$^3$H]-iloprost to $PGI_2$ receptor on human blood platelet membrane fraction Method 50 mM Tris-HCl buffer (pH 7.4) containing 15 mM $MgCl_2$, 5 mM EDTA and 10 nM [$^3$H]-iloprost were used as reaction medium. To 0.2 ml of the reaction medium, human blood platelet membrane fraction (0.3 mg protein) was added with or without a test compound. The mixture was incubated at 24° C. for 30 min. After incubation, the reaction mixture was filtered through glass fiber filter to separate bound and free [$^3$H]-iloprost. The radioactivity was counted, and bound [$^3$H]-iloprost was calculated.

Specific [$^3$H]-iloprost binding was calculated by subtracting the nonspecific binding from the total binding. Nonspecific binding was obtained by performing parallel binding experiments in the presence of non-labeled iloprost (10 µM).

The inhibitory effect of test compound was calculated from the following equation.

The percentage of inhibition (%)=100—($B_1/B_0 \times 100$)

$B_1$: specific [$^3$H]-iloprost binding in presence of test compound $B_9$: specific [$^3$H]-iloprost binding in absence of test compound The results are shown in the following table 1.

TABLE I

| Example No. | $IC_{50}$(µM) |
|---|---|
| 2 | 0.33 |
| 2(a) | 0.21 |
| 2(g) | 0.31 |
| 2(i) | 2.5 | ii) Inhibitory effect on human blood platelet aggregation

Method

Platelet-rich plasma (PRP) was prepared from human blood ($5 \times 10^5$ platelets/mm$^3$), and a test compound was added to PRP 1 min prior to the addition of ADP (4 µM). The aggregation was monitored by a change of the permeability, using a platelet aggregometer (NBS HEMA TRACER 601, Niko Bioscience, Japan).

The results are shown in the following table 2.

TABLE II

| Example No. | $IC_{50}$(µM) |
|---|---|
| 2(a) | 0.12 |
| 2(d) | 0.074 |
| 2(e) | 0.047 |
| 2(g) | 0.013 |

Toxicity

The toxicity of the compounds of the present invention is very low and therefore, it may be confirmed that the compounds of the present invention are safe for pharmaceutical use.

Application for Pharmaceuticals

The compounds of the present invention, of the formula (I) possess an agonistic activity on PGl2 receptor, and therefore are useful for the prevention and/or the treatment of thrombosis, arteriosclerosis, ischemic heart diseases, gastric ulcer and hypertension, etc.

For the purpose above described, the compounds of the formula (I), of the present invention, non-toxic salts thereof, and hydrates thereof may be normally administered systemically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 μg and 100 mg, by oral administration, up to several times per day, and between 0.1 μg and 10 mg, by parenteral administration (preferable intravenous administration), up to several times per day, or continuous administration between 1 and 24 hrs. per day from vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules.

Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents, and assisting agents for dissolving such as glutamic acid, etc.).

The tablets or pills may, if desired, be coated with a film of gastric or enteric material (such as sugar, gelatin, hydroxypropyl cellulose or hydroxypropylmethyl cellulose phthalate, etc.), or be coated with more than two films. And further, coating may include containment within capsules of absorbable materials such as gelatin.

Liquid compositions for oral administration include pharmaceutically-acceptable emulsions, solutions, syrups and elixirs. In such compositions, one or more of the active compoumd(s) is or are contained in inert diluent(s) commonly used in the art (Purified water, ethanol etc.). Besides inert diluents, such compositions may also comprise adjuvants (such as wetting agents, suspending agents, etc.), sweetening agents, flavouring agents, perfuming agents, and preserving agents.

Other compositions for oral administration included spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid, etc.). For preparation of such spray compositions, for example, the method described in the U.S. Pat. No. 2,868,691 or U.S. Pat. No. 3,095,355 (herein incorporated in their entireties by reference) may be used.

Injections for parenteral administration include sterile aqueous or non-aqueous solutions, suspensions and emulsions. Aqueous solutions, suspensions include distilled water for injection and physiological salt solution. Non-aqueous solutions, suspensions include propylene glycol, polyethylene glycol, vegetable oil such as olive oil, alcohol such as ethanol, POLYSORBATE80 (registered trade mark), etc.

Injections may comprise additional other than inert diluents: e.g. preserving agents, wetting agents, emulsifying agents, dispersing agents, stabilizing agent, assisting agents such as assisting agents for dissolving (glutamic acid, asparaginic acid, etc.).

They may be sterilized for example, by filtration through a bacteria-retaining filter, by incorporation of sterilizing agents in the compositions or by irradiation. They may also be manufactured in the form of sterile solid compositions and which may be dissolved in sterile water or some other sterile diluent(s) for injection immediately before used.

Other compositions for parenteral administration include liquids for external use, and endermic liniments, ointment, suppositories for rectal administration and pessaries for vaginal administration which comprise one or more of the active compound(s) and may be prepared by per se known methods.

Reference Examples and Examples

The following reference examples and examples illustrate the present invention, but not limit the present invention.

The solvents in parentheses show the developing or eluting solvents and the ratios of the solvents used are by volume in chromatographic separations.

Unless otherwise specified "NMR" were measured in a solution of CDCl$_3$.

Synthesis of [5-[2-[1-phenyl-1-(3-pyridyl)methylideneaminooxy]ethyl]- 5,6,7,8-tetrahydronaphthalen-1-yloxy] acetic acid methyl ester

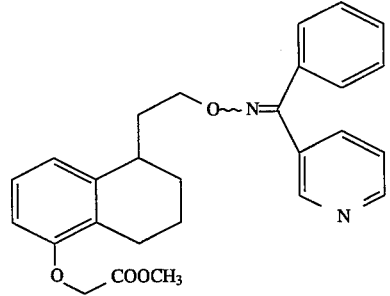

Phenyl-(2-pyridyl)methylidenehydroxylamine (269 mg) was added to a suspension of sodium hydride (34.1 mg) in dimethylformamide (3 ml), under an atmosphere of argon, at room temperature. The mixture was stirred for 30 min. The reaction mixture was added dropwise to a solution of [5-(2-bromoethyl)-5,6,7,8-tetrahydronaphthalen-1-yloxy] acetic acid methyl ester (385 mg) in dimethylformamide (5 ml). The mixture was stirred overnight. A saturated aqueous solution of ammonium chloride was added to the reaction mixture. The mixture was extracted with ether. The extract was washed with water and a saturated aqueous solution of sodium chloride, dried and evaporated. The residue was purified by silica gel column chromatography to give the title compound (463 mg) having the following physical data.

NMR: δ8.87–8.48 (3H, m), 7.88–7.56 (1 H, m), 7.56–7.15 (5H, m), 7.00 (1 H, t), 6.72 (1H, d), 6.47 (1H, d), 4.59 (2H, s), 4.30 (2H, t), 3.78 (3H, s), 3.06–2.58(3H, m), 1.96–1.46 (6H, m); MS: m/e 444(M+), 385, 371

EXAMPLE 1(a)

Synthesis of [5-[2-(diphenylmethylideneaminooxy)ethyl] -5,6,7,8 -tetrahydronaphthalen-1yloxy]acetic acid methyl ester

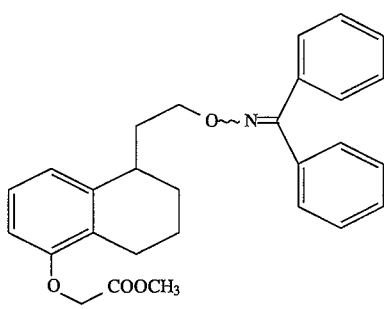

By the same procedure as described in example 1, the title compound having the following physical data was given.

TLC: Rf 0.28 (ethyl acetate:hexane=1:5); NMR: δ7.6–7.2 (10H, m), 7.03 (1 H, t), 6.78 (1 H, d), 6.50 (1 H, d), 4.62 (2H, s), 4.30 (2H, t), 3.80 (3H, s), 3.0–2.5 (3H, m), 2.2–1.6 (6H, m)

EXAMPLE 2

Synthesis of [5-[2-[1-phenyl-1-(3-pyridyl)methylideneaminooxy]ethyl]- 5,6,7,8-tetrahydronaphthalen-1-yloxy] acetic acid

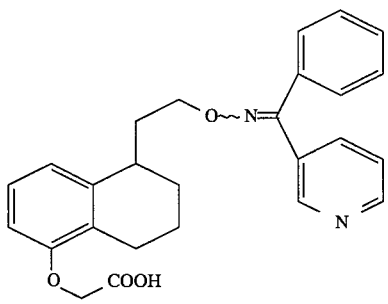

1N aqueous solution of sodium hydroxide (2 ml) was added to a mixture of the compound prepared in example 1 (460 mg) in tetrahydrofuran-methanol (6 ml+ml). The mixture was stirred for 40 min. The reaction mixture was neutralized with 1N hydrochloric acid, and extracted with ethyl acetate. The extract was washed with water and a saturated aqueous solution of sodium chloride, dried and evaporated. The residue was purified by silica gel column chromatography to give the title compound (199 mg) having the following physical data.

TLC: Rf 0.48 (methanol:methylene chloride=1:9); NMR: δ8.8–8.5 (2H, m), 7.87 and 7.77 (1 H, dd), 7.5–7.3 (6H, m), 7.1–6.9 (1H, m), 6.8–6.7 (1H, m), 6.7–6.2 (2H, m), 4.50 (2H, s), 4.30 (2H, t), 3.0–2.5 (3H, m), 2.2–1.6 (2H, m)

By the same procedure as described in example 1 and 2, using the corresponding compound, the following compounds having the following physical data was given.

EXAMPLE 2(a)

[5-[2-(diphenylmethylideneaminooxy)ethyl]-5,6,7,8-tetrahydronaphthalen-1 -yloxy]acetic acid

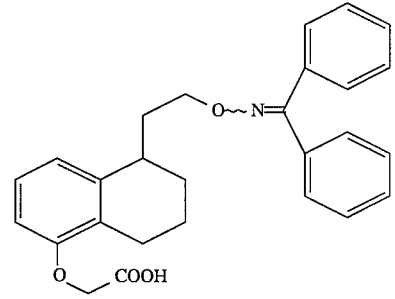

TLC: Rf 0.17 (methanol: methylene chloride=1:10); NMR: δ7.6–7.2 (10H, m), 7.05 (1 H, t), 6.80 (1 H, d), 6.53 (1 H, d), 4.65 (2H, s), 4.30 (2H, t), 3.0–2.5 (3H, m), 2.2–1.6 (6H, m)

EXAMPLE 2(b)

[1-[2-[1-phenyl-1-(3-pyridyl)methylideneaminooxy] ethyl]-2,3-dihydroinden-4yloxy] acetic acid

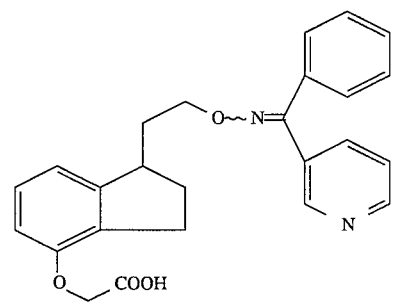

TLC: Rf 0.44 (20% MeOH/CH2Cl2); NMR: δ8.68 and 8.58 (1 H, s), 8.60 and 8.55 (1 H, d, J=7Hz), 7.85–7.81 and 7.76–7.72 (1H, m), 7.50–7.28 (6H, m), 7.13–7.04 (1 H, m), 6.88–6.80 (1H, m), 6.62–6.57 (1 H, m), 4.55 (2H, s), 4.36–4.27 (2H, m), 3.23–3.13 (1 H, m), 3.00–2.90 (1 H, m), 2.86–2.75 (1 H, m), 2.32–2.17 (2H, m), 1.85–1.63 (2H, m).

EXAMPLE 2(c)

6-[1-[1-phenyl-1-(3-pyridyl)methylideneaminooxy]methyl]-5,6,7,8 -tetrahydronaphthalen-1-yloxy]acetic acid

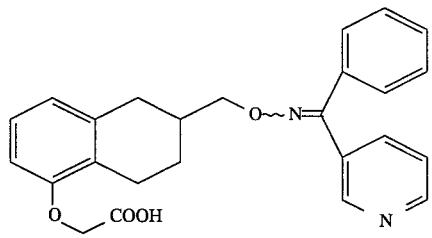

TLC: Rf 0.51 (20% MeOH/CH2Cl2); NMR: δ8.67 and 8.61 (1 H,s), 8.58 and 8.54 (1 H, d, J=7Hz), 7.85–7.79 and 7.76–7.68 (1 H, m), 7.50–7.25 (6H, m), 7.00–6.92 (1 H, m), 6.74–6.63 (1H,m), 6.59–6.50 (1H, m), 4.46 (2H, s), 4.25–4.10 (2H, m), 3.00–2.86 (1 H, m), 2.86– 2.73 (1H, m), 2.67–2.51 (1 H, m), 2.51–2.40 (1H, m), 2.23–2.12 (1 H, m), 2.00–1.87 (1H, m), 1.43–1.30 (1H, m)

EXAMPLE 2(d)

[6-[1-[1-phenyl-(3-pyridyl)methylideneaminooxy]methyl]-7,8-dihydronaphthalen-1-yloxy]acetic acid

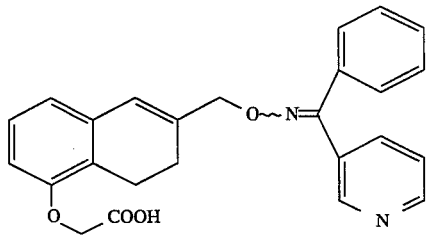

TLC: Rf 0.29 (MeOH/CH2Cl2=⅕); NMR: δ8.70–8.50 (2H, m), 7.88–7.70 (1 H, m), 7.55–7.22 (6H, m), 7.07 (1 H, t J=8Hz), 6.70 (1H, d, J=8Hz), 6.65 (1H, d, J=8Hz), 6.39 (1H, s), 4.80 (2H,s), 4.62 (2H, s), 2.91 (2H, t, J=8Hz), 2.37–2.20 (2H, s).

EXAMPLE 2(e)

[5-[2-[1,1-(3-dipyridyl)methlideneaminooxy]ethyl]-5,6,7,8-tetrahydronaphthalen-1-yloxy]acetic acid

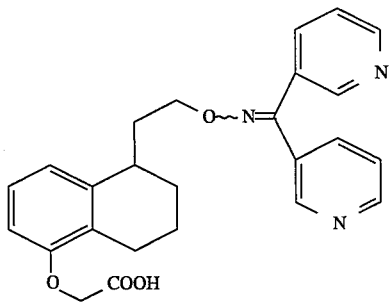

TLC: Rf 0.25 (20% MeOH/CHCl3); NMR: δ8.78–8.60 (4H, m), 7.90–7.68(2H, m), 7.60–6.50 (1 H, brs), 7.49–7.28 (2H, m), 7.03 (1H, t, J=5 Hz), 6.73 (1H, d, J=5 Hz), 6.56 (1H, d, J=5 Hz), 4.62 (2H, s), 4.34 (2H, t, J=7Hz), 2.95–2.54 (3H, m), 2.20–1.57 (6H, m).

EXAMPLE 2(f)

[5-[2-[1-phenyl-(3-pyridyl)methylideneaminooxy]ethyl]-7,8-dihydronaphthalen-1-yloxy]acetic acid

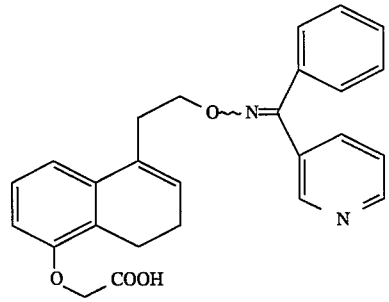

TLC: Rf 0.31 (10% MeOH/CH2Cl2); NMR: δ8.70–8.30 (2H, m), 7.70–7.60 (1H, m), 7.50–7.20 (6H, m), 7.00 (1H, t, J=8Hz), 6.93 (1 H, d, J=8Hz), 6.63 (1 H, d, J=8Hz), 5.82 (1 H, t, J=4Hz), 4.58 (2H, s), 4.27 (2H, t, J=7Hz), 2.85–2.60 (4H, m), 2.25–2.05 (2H, m)

EXAMPLE 2(g)

[5-[2-[1-phenyl-1-(3-pyridyl)methylideneaminooxy]ethyl]-7,8-dihydronaphthalen-1-yloxy]acetic acid

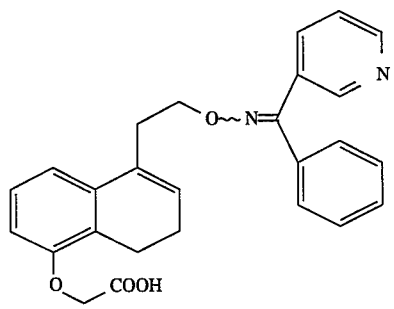

TLC: Rf 0.25 (10% MeOH/CH2C! 2) NMR: δ8.70–8.40 (2H,m), 7.85–7.75 (1 H,m), 7.50–7.20 (6H, m), 7.13 (1 H, t, J=8Hz), 6.99 (1 H, d, J=8Hz), 6.71 (1 H, d, J=8Hz), 5.92 (1 H, t, J=4Hz), 4.63 (2H, s), 4.37 (2H, t, J=7Hz), 3.00–2.65 (4H, m), 2.30–2.15 (2H, m)

Example 2(f) and 2(g) are stereo isomers, each other.

EXAMPLE 2(h)

[5-[2-[1-phenyl-1-(3-pyridyl)methylideneaminooxy]ethylidene]-5,6,7,8-tetrahydronaphthalen-1-yloxy]acetic acid

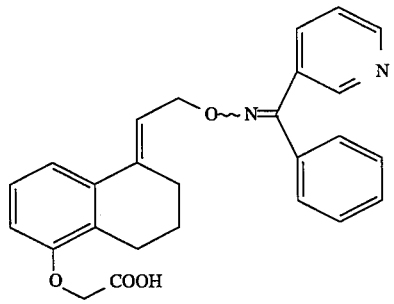

TLC: Rf 0.39 (20% MeOH/CH2Cl2); NMR: δ5 8.68–8.50 (2H,m), 7.90–7.75 (1 H, m), 7.50–7.20 (7H, m), 7.09 (1 H, t, J=8Hz), 6.66 (1 H, d, J=5 Hz), 6.27–6.16 (1 H, m), 4.93 (2H, d, J=7Hz), 4.62 (2H, s), 2.83 (2H, t, J=7Hz), 2.63–2.47 (2H, m), 1.93–1.73 (2H, m).

EXAMPLE 2(i)

[5-[3-(diphenylmethylideneaminooxy)-1-propenyl]-5,6,7,8-tetrahydronaphthalen-1-yloxy]acetic acid

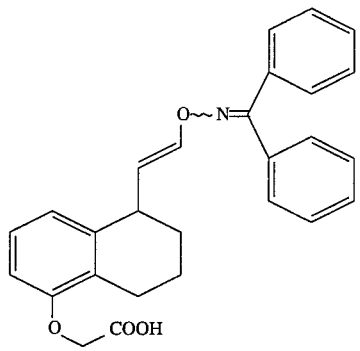

TLC: Rf 0.38 (20%MeOH/CH2Cl2); NMR: δ7.60–7.20 (10H, m), 7.12 (1 H, t), 6.82 (1 H, d), 6.59 (1 H, d), 5.80 (1 H, dd), 5.53 (1 H, dt), 4.61 (2H, s), 4.31 (2H, d), 3.84 (1 H, m), 2.75(2H, m), 2.00– 1.70 (4H, m).

Formulation Example 1

The following components were admixed in conventional method and punched out to obtain 100 tablets each containing 5 mg of active ingredient.

| | | |
|---|---|---|
| • | [5-[2-[1-phenyl-1-(3-pyridyl)methylideneaminooxy]ethyl]-5,6,7,8-tetrahydronaphthalen-1-yloxy]acetic acid | 500 mg |
| • | Carboxymethylcellulose calcium | 200 mg |
| • | Magnesium stearate | 100 mg |
| • | Micro crystalline cellulose | 9.2 g |

Formulation Example 2

The following components were admixed in conventional manner. The solution was sterilized in conventional manner, placed 10 ml portion into ampoules and freeze-dried to obtain 100 ampoules each containing 2 mg of the active ingredient.

| | | |
|---|---|---|
| • | [5-[2-[1-phenyl-1-(3-pyridyl)methylideneaminooxy]ethyl]-5,6,7,8-tetrahydronaphthalen-1-yloxy]acetic acid | 200 mg |
| • | Mannit | 50 mg |
| • | Distilled water | 1000 ml |

What is claimed is:
1. An oxime derivative of the formula (I):

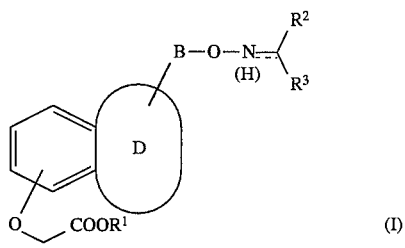

-continued
wherein

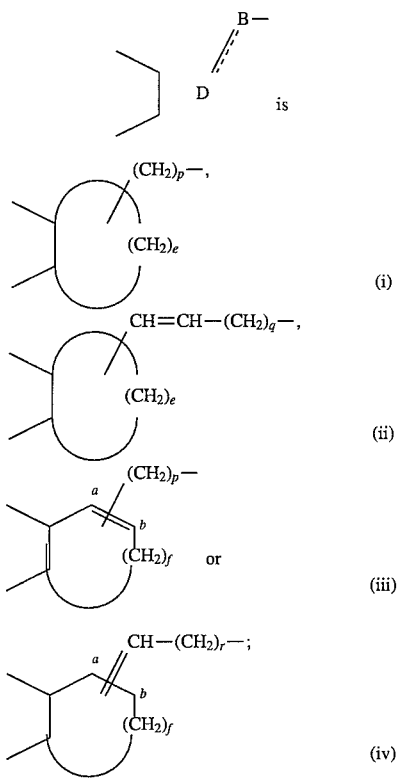

$R^1$ is hydrogen or C1–4 alkyl;
$R^2$ is
  (i) hydrogen,
  (ii) C1–8 alkyl,
  (iii) phenyl or C4–7 cycloalkyl, p2 (iv) 4–7 membered monocyclic ring containing one nitrogen,
  (v) C1–4 alkyl substituted by a benzene ring or C4–7 cycloalkyl or
  (vi) C1–4 alkyl substituted by a 4–7 membered monocyclic ring containing one nitrogen;
$R^3$ is
  (i) C1–8 alkyl,
  (ii) phenyl or C4–7 cycloalkyl,
  (iii) 4–7 membered monocyclic ring containing one nitrogen,
  (iv) C1–4 alkyl substituted by a benzene ring or C4–7 cycloalkyl or
  (v) C1–4 alkyl substituted by a 4–7 membered monocyclic ring containing one nitrogen;
e is 3–5, f is 1–3, p is 1–4, q is 1 or 2, r is 1–3; with the proviso that, when

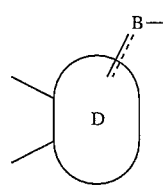

is (iii) or (iv), $-(CH_2)_p-$ and $=CH-(CH_2)_s-$ are bonded at the position a or b on the ring, and the ring in $R^2$ and $R^3$ may be substituted by one to three of C1–4 alkyl, C1–4 alkoxy, halogen, nitro or trihalomethyl; and non-toxic salts thereof.

2. A compound according to claim 1, wherein the formula:

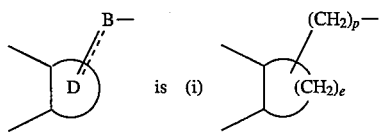

3. A compound according to claim 1, wherein the formula:

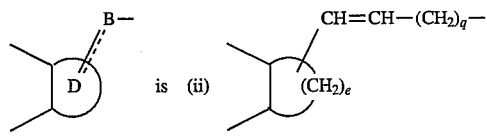

4. A compound according to claim 1, wherein the formula:

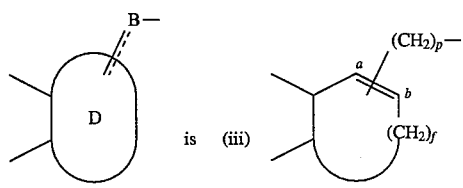

5. A compound according to claim 1, wherein the formula:

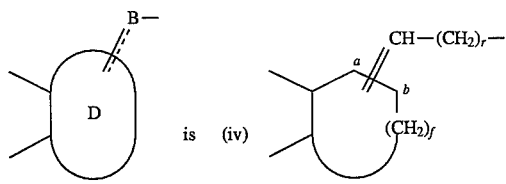

6. A compound according to claim 1, wherein $R^2$ is C1–8 alkyl.

7. A compound according to claim 1, wherein $R^2$ is phenyl or C4–7 cycloalkyl.

8. A compound according to claim 1, wherein $R^2$ is heterocyclic mono-ring of 4–7 membered containing one nitrogen.

9. A compound according to claim 1, wherein $R^2$ is a pyridine ring.

10. A compound according to claim 1, wherein $R^2$ is C1–4 alkyl substituted by phenyl or C4–7 cycloalkyl.

11. A compound according to claim 1, wherein $R^2$ is C1–4 alkyl substituted by a heterocyclic mono-ring of 4–7 members containing one nitrogen.

12. A compound according to claim 1, which is:

[5-[2-[1-phenyl-1-(3-pyridyl)methylideneaminooxy] ethyl]-5,6,7,8 -tetrahydronaphthalen-1-yloxy]acetic acid,

[5-[2-(diphenylmethylideneaminooxy)ethyl]-5,6,7,8-tetrahydronaphthalen-1 -yloxy]acetic acid,

[1-[2-[1-phenyl-1-(3-pyridyl)methylideneaminooxy] ethyl]-2,3 -dihydroinden-4acetic acid,

[6-[1-[1-phenyl-1-(3-pyridyl)methylideneaminooxy]methyl]-5,6,7,8 -tetrahydronaphthalen-1-yloxy]acetic acid,

[6-[1-[1-phenyl-(3-pyridyl)]methylideneaminooxy]methyl]-7,8 -dihydronaphthalen-1-yloxy]acetic acid,

[5-[2-[1,1-(3-dipyridyl)methylideneaminooxy]ethyl]-5,6,7,8 -tetrahydronaphthalen-1-yloxy]acetic acid,

[5-[2-[1-phenyl-1-(3-pyridyl)methylideneaminooxy] ethyl]-7,8 -dihydronaphthalen-1-yloxy]acetic acid,

[5-[2-[1-phenyl-1-(3-pyridyl)methylideneaminooxyethylidene]-5,6,7,8 -tetrahydronaphthalen-1-yloxy]acetic acid or

[5-[3-(diphenylmethylideneaminooxy)-1-propenyl]-5,6,7,8 -tetrahydronaphthalen-1-yloxy]acetic acid.

13. A pharmaceutical composition which comprises, as active ingredient, an effective amount of a compound of the formula (I) depicted in claim 1 or a pharmaceutically acceptable salt thereof, with a pharmaceutical carrier or coating.

14. A method for the treatment of thrombosis, arteriosclerosis, ischemic heart diseases, gastric ulcer or hypertension, which comprises the administration of an effective amount of a compound of the formula (I) depicted in claim 1 or a pharmaceutically acceptable salt.

* * * * *

UNITED STATES PATENT AND TRADEMARK OFFICE
CERTIFICATE OF CORRECTION

PATENT NO. : 5,480,998  Page 1 of 2
DATED : January 2, 1996
INVENTOR(S) : Nobuyuki Hamanaka It is certified that error appears in the above-indentified patent and that said Letters Patent is hereby corrected as shown below:

In column 14, between lines 30 and and 32 insert --Example 1-- just above paragraph that reads Synthesis of [5-[2-[1-phenyl-1-(3-pyridyl)methylidene- Column 19,
Claim 1, formula (I),

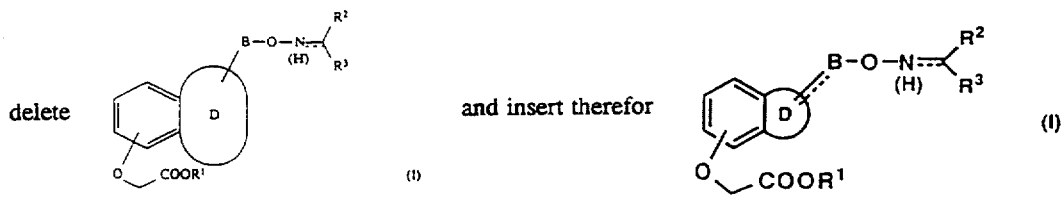

Formula (I) continued, column 20, line 4 - 9:

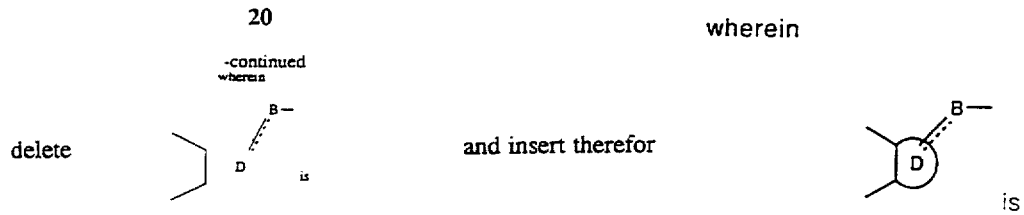

UNITED STATES PATENT AND TRADEMARK OFFICE
CERTIFICATE OF CORRECTION

PATENT NO. : 5,480,998
DATED : January 2, 1996
INVENTOR(S) : Nobuyuki Hamanaka

It is certified that error appears in the above-indentified patent and that said Letters Patent is hereby corrected as shown below:

Formula (iii),

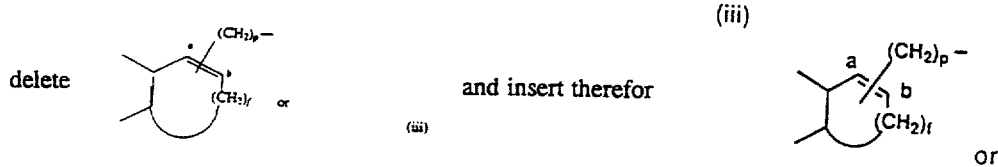

Line 38, delete "p2" immediately after "cycloalkyl," and before "(iv)"

Signed and Sealed this

Seventeenth Day of September, 1996

Attest:

BRUCE LEHMAN

Attesting Officer     Commissioner of Patents and Trademarks